US005086072A

United States Patent [19]

Trullas et al.

[11] Patent Number: 5,086,072

[45] Date of Patent: Feb. 4, 1992

[54] TREATMENT OF MOOD DISORDERS WITH FUNCTIONAL ANTAGONISTS OF THE GLYCINE/NMDA RECEPTOR COMPLEX

[75] Inventors: Ramon Trullas, Bethesda; Phil Skolnick, Potomac, both of Md.

[73] Assignee: The United States of America as represented by the Department of Health and Human Services, Washington, D.C.

[21] Appl. No.: 541,032

[22] Filed: Jun. 18, 1990

[51] Int. Cl.[5] .................... A61K 31/215; A61K 31/19

[52] U.S. Cl. .................................... 514/531; 514/557

[58] Field of Search .............................. 514/531, 557

[56] References Cited

PUBLICATIONS

Foster, A. C. et al., Nature, vol. 329, 395-396 (1987).

Kleckner et al, Science, vol. 241, 835-837 (1988).

Marvizon et al, J. Neurochem., vol. 52, 992-994 (1989).

Olney, J. B. Biol. Psychiatry, vol. 26, 505-525 (1989).

Skolnick et al, Life Sciences, vol. 45, 1647-1655 (1989).

Trullas et al, Europ. Journ. of Pharmac., vol. 185, 1-10 (1990).

*Primary Examiner*—Frederick E. Waddell
*Assistant Examiner*—Terry L. Wilson
*Attorney, Agent, or Firm*—Birch, Stewart, Kolasch & Birch

[57] ABSTRACT

A method is disclosed for the treatment of mood disorders, including major depression, by administering an effective mood disorder treating amount of a compound possessing functional antagonist properties for the N-methyl-D-aspartate receptor complex.

10 Claims, 2 Drawing Sheets

TREATMENT OF MOOD DISORDERS WITH FUNCTIONAL ANTAGONISTS OF THE GLYCINE/NMDA RECEPTOR COMPLEX

FIELD OF THE INVENTION

The present invention is concerned with the treatment of mood disorders in patients. More specifically, the present invention is concerned with the treatment of mood disorders, including major depressions, utilizing a class of compounds which possess functional antagonist properties at the N-methyl-D-aspartate (NMDA) receptor complex.

BACKGROUND OF THE INVENTION

The N-methyl-D-aspartate (NMDA) subtype of glutamate receptor and its associated cation channel are allosterically coupled to a strychnine-insensitive glycine receptor, forming a "supramolecular complex" (1). Excessive activation of this "supramolecular complex" has been linked to various neuropsychopharmacological disorders including seizure disorders, ischemic brain damage, and other neuropathologies. Both structural requirements for ligand binding to strychnine-insensitive glycine receptors on this "supramolecular complex" and their regional distribution in the central nervous system have been reported to differ remarkably from strychnine-sensitive glycine receptors. It has also been reported that there is an absolute requirement that there be present glycine for activation of NMDA receptor complexes as expressed in *Xenopus oocytes* (19).

Skolnick et al, in copending U.S. patent application Ser. No. 07/390,745, filed on Aug. 8, 1989, discloses a method of treating neuropharmacological disorders which result from excessive activation of the NMDA-receptor complex, by administering to a patient an effective neuropsychopharmacological disorder-treating amount of a compound possessing partial agonist properties for the strychnine-insensitive glycine modulatory site of the NMDA-receptor complex. Suitable partial agonists of the NMDA-receptor complex, disclosed by Skolnick et al, include 1-aminocyclopropanecarboxylic acid, and derivatives thereof. Copending U.S. patent application Ser. No. 07/390,745, filed on Aug. 8, 1989, is incorporated herein by reference.

1-Aminocyclopropane-carboxylic acid (ACPC) has been shown to be a potent and selective partial agonist of the strychnine-insensitive glycine binding site of the NMDA-receptor complex (12). The compound 2-amino-7-phosphonoheptanoic acid has been reported to be a competitive antagonist at the NMDA receptor complex (Perkins, 981) reviewed in (1). The compound (+)-5-methyl-1? ,11-dihydro-5H-dibenzo[a,d]cycloheptene -5,10-imine has been reported to be a non-competitive NMDA antagonist thought to act within the NMDA-gated cation channel (11).

SUMMARY OF THE INVENTION

An object of the present invention is to treat mood disorders in patients affected therewith. Another object of the present invention is to treat major depression in patients, major depression being one of the most common of mood disorders, and being associated with an incapacitating clinical syndrome. Another object of the present invention is to treat mental disorders which are currently treated with antidepressants (e.g., panic disorders, anorexia and bulimia and obsessive-compulsive disorders). A further object of the present invention is to treat major depression and other associated mental disorders in a patient, while producing fewer side effects than those associated with currently used antidepressants (e.g., antidepressant agents which are thought to act directly through monoaminergic pathways).

In consideration of the above objects, the present invention provides for a method of treating mood disorders in a patient, which comprises administering to a patient in need thereof, an effective amount of a compound possessing functional antagonist properties at the NMDA receptor complex.

Functional antagonist compounds useful in the methods of the present invention include partial agonists at the strychnine insensitive glycine site as well as competitive and non-competitive antagonists of the NMDA receptor at other loci on the NMDA receptor complex.

Most preferably there are used partial agonists of the strychnine-insensitive glycine modulatory site of the NMDA receptor complex in the present invention as a functional antagonist. However, competitive and non-competitive antagonists at the NMDA receptor complex are also useful as functional antagonists in the present inventive methods.

Exemplary of suitable partial agonists at the strychnine-insensitive glycine modulatory site on the NMDA receptor complex, which are useful in the present invention, are compounds of Formulae I and Ia, below:

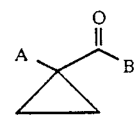

Formula I wherein A is $-NH_2$, $-NHR^1$ or $-NR^1R^2$;
B is $-OH$ or $-OR^3$;
$R^1$, $R^2$ and $R^3$, same or different, are lower alkyl and lower alkyl substituted by halogen, hydroxyl, alkoxy, oxo, mercapto, aryl or amino; or a pharmaceutically acceptable salt thereof;

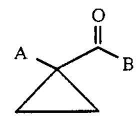

Formula Ia wherein $A^1$ is $-NH_2$, $-NHR^1$ or $-NR^1R^2$;
$B^1$ is $-OH$ or $-OR^3$;
$R^1$, $R^2$ and $R^3$, same or different are lower alkyl, or a pharmaceutically acceptable salt thereof.

Compounds possessing non-competitive or competitive antagonist properties at the NMDA receptor complex, which are useful in the present invention, include (+)-5-methyl-10,11-dihydro-5H-dibenzo[a,d]cyclopentene -5,10-imine; 2-amino-7-phosphonoheptanoic acid;2-amino-5-phosphonoheptanoic acid; Cis-4-phosphonomethyl-2-piperidine carboxylic acid; 3-[(±)-2-carboxypiperazin-4-yl]propyl-1-phosphonic acid; and pharmaceutically acceptable salts thereof.

The following Glossary of Terms is provided to remove any ambiguity which may exist as to the meaning of certain terms as used herein.

The term "functional antagonist" as used herein, means any compound which possesses pharmaceutically efficacious properties in humans, and which reduces excessive activity at NMDA operated cation channels. Such functional antagonists include compounds possessing competitive and non-competitive antagonist properties at the NMDA receptor complex, as well as compounds possessing partial agonist properties for the strychnine-insensitive glycine modulatory site of the NMDA receptor complex.

The term "a compound possessing partial agonist properties" as used herein, means a compound having partial agonist properties, when compared with the endogenous neurotransmitter glycine. Exemplary of such compounds are compounds encompassed by Formulae I and Ia as provided for herein, which compounds are derivatives of 1-aminocyclopropanecarboxylic acid.

The term "a compound possessing competitive antagonist properties at the NMDA receptor" as used herein, means a compound possessing competitive antagonist properties, when compared with the endogenous neurotransmitters glutamate and aspartate. Suitable competitive antagonist to utilize in the present invention include, for example: 2-amino-7-phosphonoheptanoic acid; 2-amino-5-phosphonopentanoic acid (42); Cis-4-phosphonomethyl-2-piperidine carboxylic acid (43); 3-[(±)-2-carboxypiperazin-4-yl]propyl-1-phosphonic acid (44); and the pharmaceutically acceptable salts thereof.

The term "a compound possessing non-competitive antagonist properties" as used herein, means a compound that reduces activity at NMDA-gated cation channels at loci other than the strychnine-insensitive glycine receptor or the NMDA receptor, as for example at sites within (inside) the cation channel itself. Suitable non-competitive antagonist to utilize in the present invention include the compound (+)-5-methyl-10, 1-dihydro-5H-dibenzo[a,d]cyclohepten 5,10-imine, and the pharmaceutically acceptable salts thereof.

The term "mood disorder" as used herein, unless otherwise qualified, means a mood disorder resulting from or associated with excess activation of the NMDA receptor complex. Exemplary of specific mood disorders included within the definition are major depression, bipolar disorder, dysthymia, seasonal affective disorder, or the like.

The term "lower alkyl" as used herein, means an alkyl radical having 1-8 carbon atoms, which may be straight or branched, including, for example, methyl, ethyl, propyl, isopropyl, butyl, isobutyl, tertbutyl, amyl, isoamyl, hexyl, heptyl, octyl, or the like.

The term "halogen" as used herein, refers to fluorine, chlorine, bromine, and iodine atoms.

The term "hydroxyl" as used herein, means —OH.

The term "lower alkoxy" as used herein, means lower alkyl—O—.

The term "oxo" as used herein, means an =O group.

The term "mercapto" as used herein, means a —SH group.

The term "aryl" as used herein, means an organic radical derived from an aromatic hydrocarbon, e.g., phenyl from benzene.

The term "amino" as used herein, means $—NH_2$.

The term "amino protecting group" as used herein, in synthesis methods means an aoyl or benzoyl radical, or the like.

The term "pharmaceutically acceptable salt" as used herein, includes acid addition salts, ammonium salts, hydrates, alcolates, and other salts of the compounds possessing functional antagonist properties disclosed herein, which salts are physiologically compatible in warm blooded animals. The acid addition salts may be formed by either strong or weak acids. Representative of strong acids are hydrochloric, sulfuric and phosphoric. Representative of weak acids are fumaric maleic, succinic, oxalic, citric, tartaric, cyclohexaminic and the like.

The following list of abbreviations utilized herein is also provided to remove any ambiguity which may exist to their meanings.

(1) N-methyl-D-aspartate, NMDA;
(2) 1-aminocyclopropanecarboxylic acid, ACPC;
(3) methyl 1-aminocyclopropanecarboxylate, ACPCM;
(4) ethyl 1-aminocyclopropanecarboxylate, ACPCE;
(5) (+)-5-methyl-10,11-dihydro-5H-dibenzo[a,d]cycloheptene-5, 10-imine, MK-801;
(6) 2-amino-7-phosphonoheptanoic acid, AP-7;
(7) 2-amino-5-phosphonoheptanoic acid, AP-5;
(8) cis-4-phosphonomethyl-2-piperidine carboxylic acid, CG5-19755; and
(9) 3-[(+)-2-carboxypiperazin-4-yl]propyl-1-phosphonic acid, NPC-12626.

BRIEF DESCRIPTION OF THE DRAWINGS

The present invention will become more fully understood from the detailed description given here and below and the accompanying drawings which are given by way of illustration only, and thus, are not limitative of the present invention, and wherein.

DETAILED DESCRIPTION OF THE INVENTION

Figure 1A:
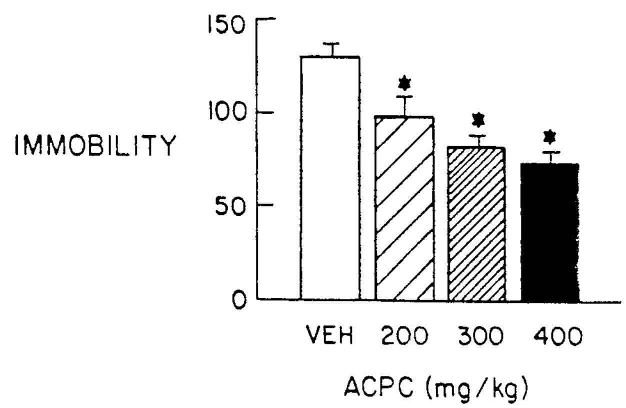
FIG. 1A and FIG. 1B—Effects of 1-aminocyclopropanecarboxylic acid on the duration of immobility in the forced swim test and ambulatory time in an open field.

The following detailed description of the invention is provided to aid those skilled in the art in practicing the present invention. Even so, the following detailed description of the invention should not be construed to unduly limit the present invention, as modifications and variations in the procedures and examples provided herein, may be made by those skilled in the art, without departing from the spirit or scope of the present inventive discovery.

The present invention is concerned with treating mood disorders associated with excessive activation of the NMDA receptor complex. More specifically, however, it is concerned with utilizing functional antagonists of this supramolecular complex to treat such mood disorders. By administering such functional antagonists of the NMDA receptor complex, it is envisioned that one may, with the methods of the present invention treat mood disorders, associated with or resulting from excessive activation of the NMDA receptor complex. Furthermore, it is provided that if one utilizes a partial agonist at the strychnine insensitive glycine receptor as the functional antagonist, as herein taught, one may treat such mood disorders without producing possible unwanted side effects, which can occur when total blockage of the NMDA receptor complex is achieved or maintained. Possible side effects avoided by utilizing the herein disclosed partial agonist (versus competitive and non-competitive antagonist of the NMDA receptor) would include, for example, schizophrenia-like symptoms in patients, loss of normal NMDA receptor mediated synaptic plasticity (which can possibly affect learning and memory in a patient), amnesia, confusional states, and muscle relaxation.

Exemplary of preferred partial agonist to use in the present invention include those compounds of Formulae I and Ia, which are disclosed herein. Such compounds can be commercially purchased or can be prepared by methods readily known and understood by those skilled in the art. For example, lower alkyl esters of 1-aminocyclo-propanecarboxylic acid can be prepared by Fischer esterification of the parent compound. Additionally, for example, compounds of Formulae I or Ia wherein "A" is a lower alkyl amino or lower -dialkyl amino moiety, can be easily prepared by reacting 1-aminocyclopropanecarboxylic acid lower alkyl esters with desired lower alkyl halides, while protecting sites on the amino moiety with "amino protection groups", when needed and deprotecting there-after by usual means.

While total blockage of the NMDA receptor complex may occur if powerful competitive or non-competitive antagonists are utilized in the present invention, this does not prevent such compounds from being encompassed by the present invention. In this regard, it is noted that each of the functional antagonists of the NMDA receptor complex encompassed hereby, possesses the ability to regulate overactivation of the complex, and thus each of the same are effective in treating mood disorders.

Regarding the availability of certain competitive and non-competitive antagonists useful in the present invention, it is noted that 2-amino-7-phosphanoheptanoic acid (AP-7) is commercially available from Research Biochemical Inc., (RBI) or Tocris Neuramin. A method of preparation for (+)-5-methyl-10,11-dihydro-5H-dibenzo[a,d]cyclohepetene-5,10-imine(MK-801) is provided for by Anderson et al in U.K. Patent document GB 2,004,873B (1982), incorporated herein by reference. With respect to the competitive NMDA receptor antagonists, AP-5, CG5-19755 and NPC-12626, synthesis methods for preparing the same, have been previously reported in the literature, and/or synthesis methods for their preparation are readily ascertainable to those of ordinary skill in the art.

The following discussions are divided into sections relating to "Pharmacology" and "Pharmaceutical Compositions". In the following "Pharmacology" section, pharmacological testing and results are discussed, which testing and results evidence the advantageous ability of the functional antagonist of the NMDA receptor complex, herein encompassed, to treat mood disorders. In the "Pharmacology" section, there also occurs a detailed description in accompanying FIGS. 1, 2A and 2B. In the following "Pharmaceutical Compositions" section, there are provided dosages and methods for the functional antagonists encompassed by the present invention, to aid those skilled in the art in treating mood disorders therewith.

Pharmacology

Activation of the N-methyl-D-Aspartate (NMDA) receptor complex (1) is required for the development of a lasting increase in synaptic efficacy known as long term potentiation (LTP) in specific regions of the central nervous system (2,3). Exposure to inescapable, but not escapable stress has recently been shown to impair the induction of LTP in the CAI layer of hippocampus (4), an area containing a high density of NMDA receptors (5,6). Since inescapable stress also induces a syndrome of behavioral depression that is antagonized by clinically effective antidepressants (7), we hypothesized that the NMDA receptor complex could also be involved in mood disorders, including behavioral deficits induced by stress. This novel hypothesis was tested by evaluating functional antagonists of the strychnine-insensitive glycine modulatory site in animal models commonly used to detect clinically effective antidepressants. (8, 9)

Upon the completion of such testing, we discovered that a competitive NMDA antagonist such as 2-amino-7-phosphonoheptanoic acid (10), a non-competitive antagonist such as (±)-5-methyl-10, 1-dihydro-5H-dibenzo[a,d]cycloheptene5,10-imine (11), and partial agonists at the strychnineglycine modulatory site such as 1-aminocyclopropanecarboxylic acid (12) mimic clinically effective antidepressants in these models. Such pharmacological testing thus revealing that functional antagonists of the NMDA receptor complex may represent a new class of mood disorder treating agents (e.g., antidepressant agents, etc.).

Certain exemplary compounds encompassed hereby were evaluated pharmacologically in mice using the forced swim (8) and/or tail suspension (9) tests. These tests were initially designed to detect potential antidepressant agents (13, 14) based on the abilities of clinically effective antidepressants to reduce the immobility that animals typically display after active and unsuccessful escape attempts when subjected to these inescapable stressors. Moreover, the predictive validity (15) and pharmacological specificity (13, 14) of these tests has led to the proposal that they represent animal models of depression. (16)

The duration of immobility during the last four minutes of a six minute forced swim was measured in male NIH/HSD mice (25-30 g) as described by Porsolt et al (8), AP-7 produced a significant, dose dependent reduction in the duration of immobility in the forced swim test [$F(4,71) = 17$, $p<0.0001$] without affecting ambulatory time (a measure of motor activity) in an open field (see Table 1 below). MK-801 (11,17) also reduced significantly the duration of immobility in this test. This effect was biphasic (Table 1), with the maximum reduction (92% at 0.5 mg/kg) corresponding to a parallel increase (34%) in ambulatory time in an open field. However, other doses of MK-801 (0.1 and 1 mg/kg) that significantly reduced the duration of immobility (43-54%) did not alter ambulatory time (see Table 1 below).

Figure 1B:
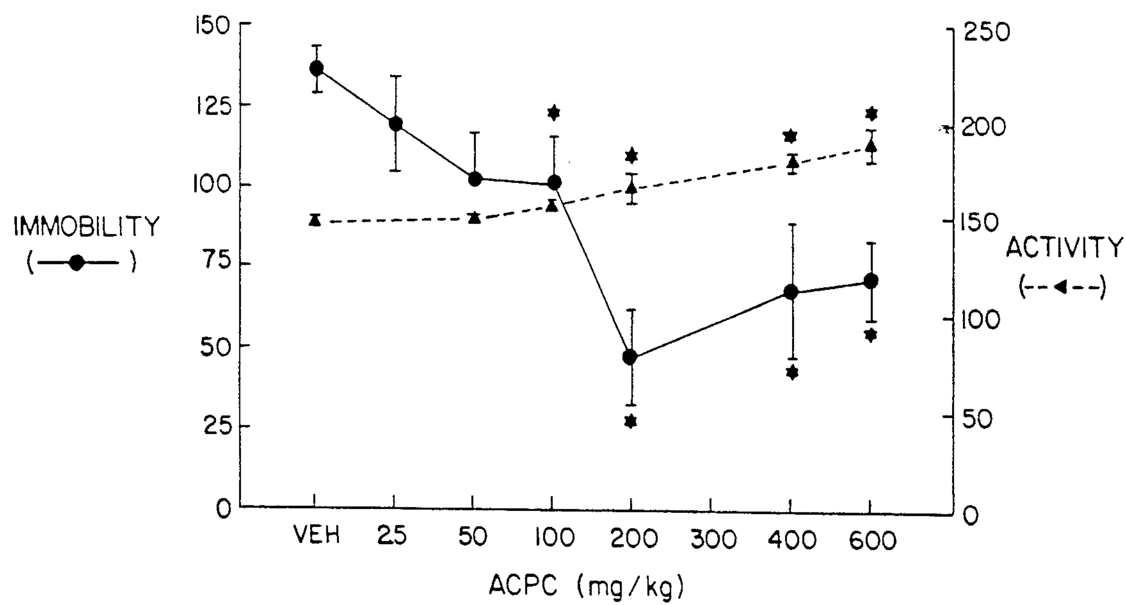

Glycine has been reported to augment transmission at NMDA-gated cation channels (18) through an allosteric action at strychnine-insensitive glycine receptors, and more recent studies in both Xenoous oocytes (19) and primary cultures of rat visual cortex (20), indicate that glycine may be an absolute requirement for the operation of NMDA-gated cation channels. We hypothesized that a high affinity partial agonist ligand at strychnine-insensitive glycine sites could function as an NMDA antagonist and thus be effective in the present inventive treatment methods. To test this hypothesis, we used ACPC, a high affinity ligand ($K_i \sim 32$ nM) at strychnine-insensitive glycine receptors that is significantly less efficacious than glycine in stimulating [$^3$H]MK-801 binding (12) to sites within the NMDA-gated cation channel. We determined that ACPC reduced immobility in the forced swim test in a dosedependent fashion [$F(6,94)=7$, $p<0.0001$], with the maximum reduction (65%) manifest at a dose of 200 mg/kg (FIG. 1). While ACPC also produced modest (29% at 600 mg/kg) but statistically significant increases in ambulatory time [$F(5,60)=10$, $p<0.0001$], this action appears unrelated to the reduction in immobility observed in the forced swim test. Thus, significant effects on immobility were manifest at doses that did not alter ambulatory time, and no further reductions in immobility were observed at doses (>200 mg/kg) which continued to increase the time spent in ambulation (FIG. 1).

Figure 2A:
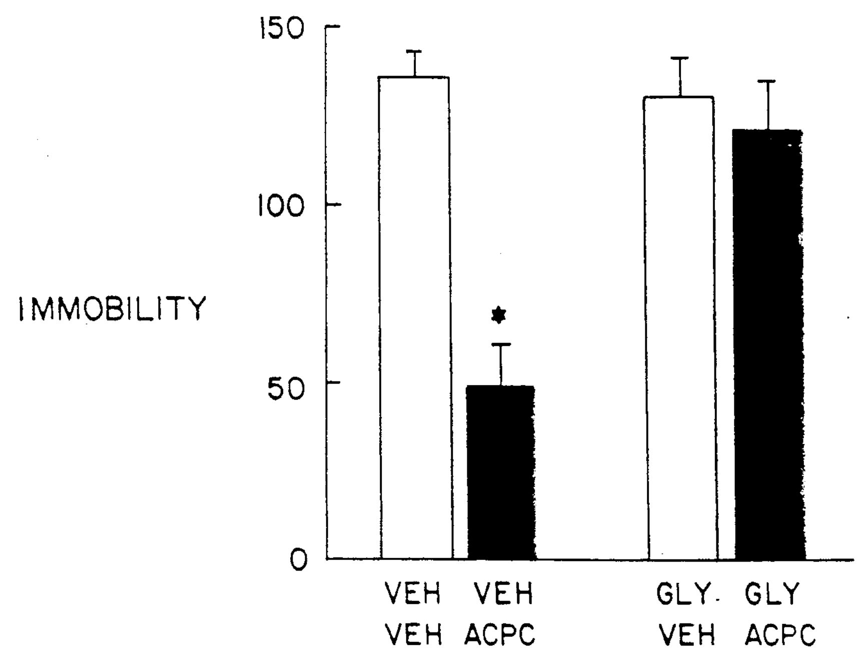
FIG. 2A—Effects of glycine on the pharmacological actions of 1-aminocyclopropanecarboxylic acid (duration of immobility in the forced swim test)
Figure 2B:
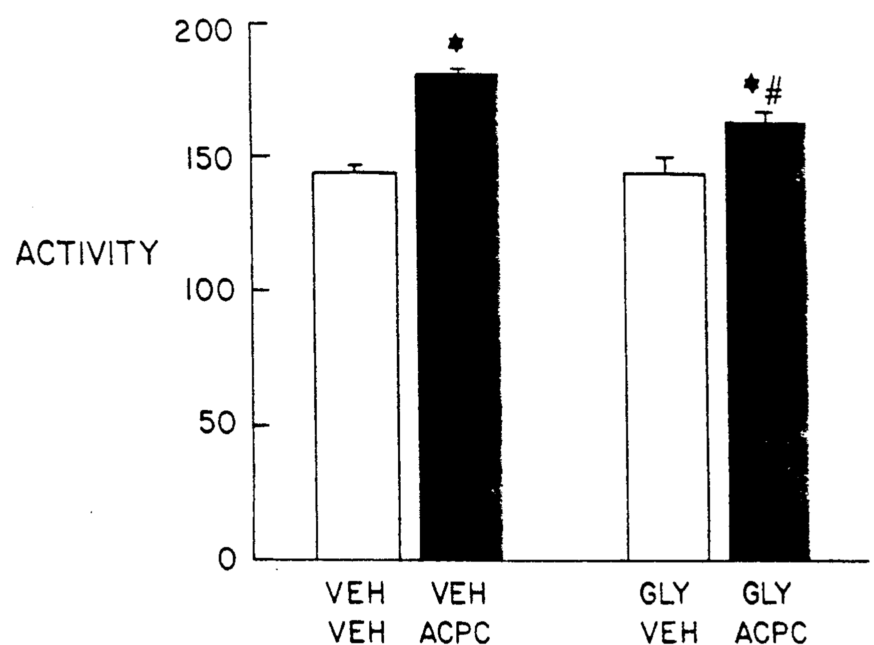
FIG. 2B—Effects of glycine on the pharmacological actions of 1-aminocyclopropanecarboxylic acid (ambulatory time in an open field test).

We further hypothesized that if the pharmacological actions of ACPC are produced by a partial agonist action at strychnine-insensitive glycine receptors, these effects should be blunted or abolished by elevating glycine concentrations in the brain. Thus, upon parenteral administration of glycine (800 mg/kg), there was completely abolished the effect of ACPC (400 mg/kg) in the forced swim test (FIG. 2A), and partial antagonism of the locomotor effects of ACPC in the open field (FIG. 2B). This dose of glycine was devoid of intrinsic activity in these behavioral measures (FIG. 2) but was sufficient to raise glycine levels in the hippocampus [an area with a high density of strychnine-insensitive glycine receptors (21)]by 62% (FIG. 2, legend). These observations, coupled with the very low affinity ($IC_{50}>1$ mM) of ACPC for strychnine sensitive glycine receptors (12) suggest that the pharmacological actions of ACPC are mediated through strychnineinsensitive glycine receptors coupled to NMDA-gated cation channels.

The effects of ACPC were also examined in the tail suspension test [another animal model used to evaluate potential antidepressant agents (9)], since the predictive validity of the forced swim test as a means of detecting antidepressants may be lower in mice than in rats (22). In this model, acute administration of clinically effective antidepressants has been reported to reduce the immobility observed in mice during a six minute period of tail suspension (9). In C57Bl/6J mice, chosen for their high basal immobility scores in this test relative to other strains (23). ACPC produced a dose dependent [$F(2,31)=29$, $p<0.0001$] reduction in immobility (FIG. 1, inset).

Based on results obtained with 1-aminocyclopropanecarboxylic acid in the above test procedures that are highly predictive of antidepressive activity in man (8,9, 13, 14), it is provided herein that derivatives thereof, by Formulae I and Ia are effective in treating mood disorders, and more specifically are pharmacologically active antidepressive agents. Exemplary of efficacious compounds useful in the present invention, which are encompassed by Formulae I and Ia are 1-aminocyclopropanecarboxylic acid, 1-aminocyclopropanecarboxylic acid methyl ester, 1-aminocyclopropenecarboxylic acid ethyl ester, and pharmaceutically acceptable salts thereof, among others.

To further evidence the effectiveness of compounds of Formulas I and Ia in the methods of the present invention, scientific test results are also provided in Table 2 below. Such results show the effects of 1-aminocyclopropanecarboxylic acid and its methyl ester (ACPCM) on swim induced immobility, as described in the legend to Table 1, below. The scientific results provided in Table 2, show that the minimum effective dose for ACPCM was significantly lower (50 mg/kg) than for the free acid ACPC (100 mg/kg). Based on such results contained in Table 2, it is thought that ACPCM may be one of the most efficacious and beneficial of the partial agonist compounds of Formula I or Ia, to administer to a patient for the treatment of mood disorders.

While both competitive NMDA receptor antagonists (such as AP-7) (10) and use-dependent channel blockers (noncompetitive antagonists) such as MK-801 (24) are also useful in the present inventive methods, nonetheless, certain preclinical studies using select preclinical models (25–27) have indicated a potential for undesirable side effects and low safety margins for such compounds (28-30) that could potentially restrict their use in the methods of the present invention. In contrast, substances like ACPC which only alter the activity of ligand-gated ion channels through a modulatory site are thought to possess fewer side effects and more favorable margins of safety. This is exemplified, for instance, by the actions of benzodiazepines at G-ABA-gated chloride channels (19, 31). Thus, the use of partial agonists of the strychnine-insensitive glycine modulatory site of the NMDA receptor complex represents a locus for the design of such compounds, since we have discovered that partial agonists such as ACPC, like competitive (32, 33) and non-competitive (34, 35) NMDA receptor antagonists, possesses anticonflict actions in animal models (36), but do not produce the muscle relaxation or ataxia (37) associated with these other compounds (35, 38). It is for this reason, that compounds possessing partial agonist properties for the strychnine-insensitive glycine modulatory site of the NMDA receptor complex, are thought most preferred in the present inventive methods.

The results disclosed herein demonstrate that ligands of the NMDA receptor complex can reduce the behavioral deficits produced by inescapable stressors in two animal models with efficacies comparable to clinically effective antidepressants (8, 9) (Table 1 legend; FIG. 1). Since current hypotheses on the pathophysiology of affective disorders, which have been of heuristic value, were based largely on preclinical studies of the neurochemical effects of tricyclic antidepressants (39), the ability of specific ligands of the NMDA receptor complex as disclosed herein, to mimic the actions of clinically effective antidepressants in animal models, provides evidence of a novel utility for the compounds disclosed herein.

TABLE 1

Effects of AP-7 and MK-801 on swim-induced immobility and ambulatory acitivity in an open field

| DRUG | DOSE | IMMOBILTY | % | ACTIVITY | % |
|---|---|---|---|---|---|
| Con- | — | 144 ± 6 (28) | | 145 ± 5 (9) | |
| trol | 40 | 141 ± 21 (7) | | 144 ± 5 (4) | |
| AP-7 | 80 | 153 ± 9 (10) | | 167 ± 16 (3) | |
| | 100 | 93 ± 8* (20) | −35 | 153 ± 5 (11) | |
| | 200 | 55 ± 13*# (11) | −62 | 134 ± 10 (17) | |
| Con- | — | 140 ± 12 (8) | | 150 ± 10 (8) | |
| trol | 0.1 | 80 ± 10* (8) | −43 | 144 ± 4 (8) | |
| MK- | 0.5 | 11 ± 4*# (8) | −92 | 201 ± 3*# (8) | +34 |

TABLE 1-continued

| Effects of AP-7 and MK-801 on swim-induced immobility and ambulatory acitivity in an open field | | | | | |
|---|---|---|---|---|---|
| DRUG | DOSE | IMMOBILTY | % | ACTIVITY | % |
| 801 | 1 | 64 ± 23* (8) | −54 | 170 ± 14 (8) | |

Legend. The effects of a competitive (AP-7) and a non-competitive (MK-801) NMDA receptor antagonist on swim stress-induced immobility were investigated in NIH/HSD male mice using the procedure described by Forsolt et al (8). The duration of immobility was measured during the last 4 minutes of forced swim.
The time spend ambulating (activity) in an open field (43 × 43 × 20 cm) was measured under dim light (<50 lux in the center of the open field) for 5 minutes with a computerized activity monitor (Opto-Varimex, Columbus Instruments, Columbus, OH). MK-801 and AP-7 were administered i.p. 15 minutes and 30 minutes before testing, respectively. MK-801 was dissolved in saline. AP-7 was dissolved in 0.5N NaOH (8% of volume) and saline added to volume.
Controls received an equivalent volume of the corresponding vehicle. Values represent mean ± standard error of the mean with the number of animals in parenthesis. Doses are in mg/kg. Immobility and ambulatory activity are in seconds. Symbols: *, significantly different from the control group; #, significantly different from all other groups ($p < 0.05$, Student-Newman Keuls test).
Imipramine (10-30 mg/kg) also produced a dose dependent reduction (28-69%) in the duration of immobility in the forced swim test. These reductions in immobility are similar in magnitude to those reproted by Porsolt et al. (8)

TABLE 2

| Effects of ACPC and ACPCM on swim-induced immobility | | | |
|---|---|---|---|
| DRUG | DOSE | IMMOBILITY | % |
| Control | — | 137 ± 12 (14) | |
| ACPC-Methyl Ester | 25 | 126 ± 8 (11) | −8 |
| | 50 | 89 ± 17* (13) | −35 |
| | 100 | 40 ± 18* (3) | −71 |
| | 150 | 69 ± 10* (9) | −50 |
| Control | — | 136 ± 7 (40) | |
| ACPC | 25 | 119 ± 15 (11) | −13 |
| | 50 | 102 ± 15 (10) | −25 |
| | 100 | 101 ± 15* (10) | −26 |
| | 200 | 47 ± 15* (10) | −65 |
| | 300 | 78 ± 10* (10) | −43 |
| | 400 | 68 ± 21* (10) | −50 |
| | 600 | 71 ± 12* (10) | −48 |

Legend: Effects of ACPC-Methyl Ester and ACPC on swim-induced immobility. The duration of immobility was measured a described in Table 1. Symbols: *, significantly different from control group, $p < 0.05$, Student-Newman-Keuls. The minimum effective dose for ACPC-Methyl Ester was significantly lower (50 mg/kg) than for ACPC (100 mg/kg).

As a further aid to those desiring to practice the present invention, the following detailed description of FIGS. 1 and 2 is provided. Such Figures are based on results obtained in the animal testing models herein employed to evidence the mood disorder treating properties of the functional antagonists encompassed by the present invention.

FIGURE 1

Effects of ACPC on the duration of immobility in the forced swim test and ambulatory time in an open field.

Symbols: Circles, immobility in the forced swim test (sec.); triangles, ambulatory time (sec.) in an open field. * Significantly different from the vehicle (VEH) group, $p < 0.05$, Student-Newman-Keuls test. Values represent means ± standard error of the mean. The number of animals examined in the forced swim test was: VEH, 40; ACPC 25 mg/kg, 11 and 50–600 mg/kg, 10. In the open field, the number of animals tested was: VEH 23; 50 and 600 mg/kg, 5; and 100–400 mg/kg, 10. Male NIH/HSD mice (25–30 g) were injected i.p. with ACPC dissolved in saline. Controls received an equivalent volume of saline. Fifteen minutes later, mice were placed in a cylinder (diameter: 10 cm; height: 25 cm) filled with 6 cm of water (22°–25° C.) and the duration of immobility during the last four minutes of forced swim was measured as described. (8) The ambulatory time in an open field was measured for five minutes, fifteen minutes after injection of ACPC as described in Table 1.

Inset: Effects of ACPC on tail suspension-induced immobility. Values are mean standard error of immobility (sec.) during a 6 minute test. The number of animals used in this test was: VEH, 16; ACPC, 200 mg/kg, 6; 300 mg/kg, 9 and 400 mg/kg, 7. Male C57Bl/6J mice [20–25 g](Jackson Laboratories, Bar Harbor, ME) were injected with ACPC. Fifteen minutes later, mice were suspended by the tail and the duration of immobility measured as described. (9, 23) The highest dose of ACPC used (400 mg/kg) produced a modest increase in ambulatory time (18%) in the open field. Several competitive antagonists at strychnine-insensitive glycine receptors did not reduce immobility in the forced swim test. 7-chlorokynurenic acid (25–150 mg/kg), indole2-carboxylic acid (I2CA) (25–200 mg/kg), 3-amino-1-hydroxypyrrolidone (HA-966) (2.5-10 mg/kg), cycloleucine (100–400 mg/kg) and 1-aminocyclobutanecarboxylic acid (ACBC) (50–100 mg/kg) were tested under identical conditions to those employed for the other agents (Table 1 and FIG. 1). However, several of these compounds (HA-966, I2CA, ACBC) produced marked behavioral effects, including ataxia, that were evident prior to forced swim which could interfere with performance in this test. Moreover, several of the compounds (I2CA, HA-966) were lethal when combined with forced swim. The relatively low affinities of these compounds for the strychnine-insensitive glycine receptor (compared to glycine) together with poor penetration into the central nervous system, may also contribute to their lack of effect in the forced swim test.

FIGURES 2A AND 2B

Effects of glycine on the pharmacological actions of ACPC. Duration of immobility (sec.) over the last four minutes of the forced swim test (FIG. 2A), and ambulatory time in an open field during a five minute test (FIG. 2B). Ten mice were used in each group.

Symbols: *, significantly different from the corresponding vehicle group, #, significantly different from the vehicle-ACPC group ($p < 0.05$, Student-Newman-Keuls test). Glycine (800 mg/kg) or an equivalent volume of saline was administered intraperitoneally to NIH/HSD mice 45 minutes prior to ACPC (400 mg/kg). Fifteen minutes after ACPC administration, animals were evaluated in the forced swim test or in an open field as described in Table 1. This dose of glycine was selected based on a previous report (40), showing that parenteral administration of large doses is required to elevate cerebral levels of glycine. In a parallel series of experiments, glycine concentrations in the hippocampus [which contains a high density of strychnine-insensitive glycine receptors (21)] were elevated by 62% (from 0.69±0.02 to 1.12±0.05 μmol/g) 60 minutes after i.p. administration of 800 mg/kg of glycine. The concentrations of other amino acids (such as glutamate, serine, taurine, GABA and alanine) were unchanged (data not shown). Amino acid levels were determined using HPLC/EC with an isocratic separation method and pre-column amino acid derivatization with o-pthalaldehyde and β-mercaptoethano (41).

Pharmaceutical Compositions

The functional antagonists encompassed by the present invention may be formulated into sterile pharmaceutical compositions for injection, by combination with appropriate pharmaceutically acceptable carriers or diluents, or may be formulated into preparations in liquid or solid forms for usual routes of administration (e.g., oral administration). The following methods and excipients are therefore merely exemplary and are in no way to be construed as limiting the present inventive methods.

In pharmaceutical dosage forms, functional antagonists encompassed by the present invention may be used in the form of their pharmaceutically acceptable salts, and also may be used alone or in appropriate association, as well as in combination with other pharmaceutically active compounds.

When injectable compositions are desired, the functional antagonists of the present invention may be formulated, for example, into preparations for injection by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Alternatively, if one wishes to prepare an oral dosage form containing one of the functional antagonists herein encompassed, commonly used and pharmaceutically acceptable tabletting excipients, such as lactose, microcrystalline cellulose, corn starch, stearic acid, or the like, may be used, if desired, to prepare such dosage forms.

The amount of the compounds of the present invention to be used may vary according to the severity and type of mood disorders encountered, as well as the amount to excess NMDA receptor activation encountered. Nonetheless, when the compounds of the present invention are injected, a suitable dosage is thought to be about 0.1 to 20 mg/kg body weight, and preferably 2 to 10 mg/kg body weight. The most preferred dosage is, of course, that amount sufficient to render controllable the mood disorder encountered.

The functional antagonists provided herein, may be formulated into unit dosage forms, wherein the term "unit dosage" refers to physically discrete units suitable as unitary dosages for human subjects, each unit containing a predetermined quantity of a functional antagonist herein encompassed, calculated in an amount sufficient with a pharmaceutically acceptable, diluent, carrier or vehicle. The specifications for such unit dosage forms depends on the particular compound employed and the effect to be achieved, and the pharmacodynamics associates with each compound in the treated patient.

Any necessary adjustments in dose can be readily made to meet the severity of the mood disorder encountered and adjusted accordingly by the skilled practitioner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Each of the following references are incorporated herein by reference.

REFERENCES

1. Foster, A.C. & Fagg, G.E. *Nature* 329, 395-396 (1987).
Collingridge, G.L., Kehl, S.J. & McLennan, H. J. Physiol. 334, 33-46 (1983).
Harris, E.W., Ganong, A.H. & Cotman, C.W. *Brain Res.* 323, 132-137 (1984).
4. Shors, T.J., Seib, T.B., Levine, S. & Thompson, R.F. *Science* 244, 224-226 (1989).
Monaghan, D.T., Holets, V.R., Toy, D.W. & Cotman, C.W., Nature 306, 176-179 (1983).
6. Monaghan, D.T., Yao, D., Olverman, H.J., Watkins, J.C. & Cotman, C.W. *Neurosci. Lett.* 52, 252-258 (1984).
7. Shanks, N. & Anisman, H. Psychopharm. 99, 122-128 (1989).
8. Porsolt, R.D., Bertin, A. & Jalfre, M. *Arch. Int. Pharmacodyn. Ther.* 229, 327-336 (1977).
9. Steru, L., Chermat, R., Thierry, B. & Simon, P. *Psychopharm.* 85, 367-370 (1985).
10. Perkins, M.N., Stone, T.W., Collins, J.F. & Curry, K. *Neurosci. Lett.* 23, 333-336 (1981). 11. Wong, E.H.F., Kemp, J.A., Priestley, T., Knight, A.R., Woodruff, G.N. & Iversen, L.L. *Proc. Natl. Acad. Sci. USA* 83, 7104-7108 (1986).
12. Marvizon, J.C., Lewin, A.H. & Skolnick, P. *J. Neurochem.* 52, 992-994 (1989).
13. Porsolt, R.D. in *Antidepressants: Neurochemical, Behavioral and Clinical Perspectives* (eds. Enna, S.J., Malick, J.B. & Richelson, E.) 121-139 (Raven Press, New York, 1981).
14. Steru, L., Chermat, R., Thierry, B., Mico, J.A., Lenegre, A., Steru, M., Simon, P. & Porsolt, R.D. *Prog. Neurosychopharm. & Biol. Psychiat.* 11, 659-671 (1987).
15. Willner, P. *Psychopharmacology* 83, 1-16 (1984).
16. Thierry, B., Steru, L., Chermat, R. & Simon, P. Behav. Neur. Biol. 41, 180-189 (1984).
17. Huettner, J.E. & Bean, B.P. *Proc. Natl. Acad. Sci. USA* 85, 1307-13011 (1988).
18. Johnson, J.W. & Ascher, P. Nature 25, 529-531 (1987).
19. Kleckner, N.W. & Dingledine, R. Science 241, 835-837 (1988).
20. Huettner, J.E. Science 243, 1611-1613 (1989).
21. Bristow, D.R., Bowery, N.G. & Woodruff, G.N. Eur. *J. Pharm.* 126, 303-307 (1986).
22. Borsini, F. & Meli, A. Psvchopharm. 94, 147-160 (1988).
23. Trullas, R., Jackson, B. & Skolnick, P. *Psychopharm.* 99, 287-288 (1989).
24. Honey, C.R., Miljkovic, Z. & MacDonald, J.F. *Neurosci. Lett.* 61, 135-139 (1985).
25. Cavalheiro, E.A., Lehmann, J. & Turski, L. (eds.) *Frontiers in excitatory amino acid research.* (Alan R. Liss, New York, 1988.
26. Choi, D.W. *Neuron.* 1, 623-634 (1988).
27. Olney, J.B. *Biol. Psychiatry.* 26, 505-525 (1989).
28. Olney, J.W., Labruyere, J. & Price, M.T. *Science* 244, 1360-1362 (1989).
29. Rogawski, M.A., Thurkauf, A., Rice, K.C., Jacobson, A.E. & Ffrench-Mullen, J.M.H. in *Frontiers in excitatory amino acid research* (eds. Cavalheiro, E.A., Lehmann, J. & Turski, L.) 227-230 (Alan R. Liss, New York, 1988).
30. Lehmann, J., Schneider, J.A. & Williams, M. *Ann. Reo. Med. Chem.* 22, 31-40 (1987).

31. Barnard, E.A., Darlison, M.G. & Seeburg, P. *Trends Neurosci.* 10, 502-509 (1987).

Bennett, D. & Amrick, C. *Life Sci.* 39, 2455-2461 (1986).

33. Stephens, D.N., Meldrum, B.S., Weidmann, R., Schneider, C. & Grützner, *M. Psychopharm.* 90, 166-169 (1986).

34. Clineschmidt, B.V., Williams, M., Witoslawski, J.J., Bunting, P.R., Risley, E.A. & Totaro, J.A. *Drug Dev. Res.* 2, 147-163 (1982).

35. Liebman, J.M. & Bennett, D.A. in *Frontiers in excitatory amino acid research* (eds. Cavalheiro, E.A., Lehmann, J. & Turski, L) 301-308 (Alan R. Liss, New York, 1988).

36. Trullas, R., Jackson, B. & Skolnick, P. *Pharmacol. Biochem. Behav.* 34, (313-316) (1989).

37. Skolnick, P., Marvizon, J.C., Jackson, B.W., Monn, J.M., Rice, K.C. & Lewin, A.H. *Life Sci.* 45, 1647-1655 (1989).

38. Turski, L., Schwarz, M , Turski, W.A., Klockgether, T., Sontag, K-H. & Collins, J.F. *Neurosci. Lett.* 53, 321-326 (1985).

39. Siever, L.J. & Davis, K.L. *Am. J. Pschiat.* 142, 1017-1031 (1985).

40. Toth, E. & Lajtha, A. *Neurochem. Res.* 6, 1309-1317 (1981).

41. Donzanti, B.A. & Yamamoto, B.K. *Life Sci.* 43, 913-922 (1988).

42. Watkins, J. and Olverman H. *Trends in Neuroscience* 10, 265-272 (1987).

43. Murphy, D., Hutchison, A., Hurt, S., Williams, M. and Sills, M. *Brit. J. Pharmacol.* 95, 932-938 (1988).

44. Ferkany, J., Kyle, D., Willets, J., RZesZotarski, W., Guzewska, M., Ellenberger, S., Jones, S., Sacaan, A., Snell, L., Borosky, S., Jones, B., Johnson, K., Balster, R., Burchett, K., Kawasaki, K., Hoch, D. and Dingledine, R. *J. Pharmacol. Exp. Ther.* 250, 100-109 (1989).

What is claimed is:

1. A method for treating mood disorders selected from the group consisting of major depression, bipolar disorder, dysthemia, and seasonal effective disorder in a patient, which comprises:

administering to a patient in need thereof, an effective amount of a compound possessing functional antagonist properties for the N-Methyl-D-Aspartate (NMDA) receptor complex.

2. The method of claim 1, wherein said mood disorder is major depression.

3. The method of claim 1, wherein the compound which is administered possesses partial agonist properties for the strychnine-insensitive glycine modulatory site of the NMDA receptor complex.

4. The method of claim 1, wherein the compound which is administered possesses partial agonist properties for the strychnine-insensitive glycine modulatory site of the NMDA receptor complex, and is a compound having the formula:

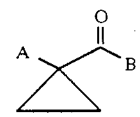

Formula I wherein

A is $-NH_2$, $-NHR^1$ or $-NR^1R^2$;

B is $-OH$ or $-OR^3$;

$R^1$, $R^2$ and $R^3$, same or different, are lower alkyl, or lower alkyl substituted by halogen, hydroxyl, alkoxy, oxo, mercapto, aryl or amino; or a pharmaceutically acceptable salt thereof.

5. The method of claim 1, wherein the compound which is administered possesses partial agonist properties for the strychnine-insensitive glycine modulatory site of the NMDA receptor complex, and is a compound having the formula:

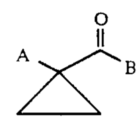

Formula Ia wherein $A^1$ is $-NH_2$, $-NHR^1$ or $-NR^1R^2$;

$B^1$ is $-OH$ or $-OR^3$;

$R^1$, $R^2$ and $R^3$, same or different are lower alkyl, or a pharmaceutically acceptable salt thereof.

6. The method of claim 4, wherein the compound is:
1-aminocyclopropanecarboxylic acid,
1-aminocyclopropanecarboxylic acid methyl ester,
1-aminocyclopropanecarboxylic acid ethyl ester, or
a pharmaceutically acceptable salt thereof.

7. The method of claim 5, wherein the compound is:
1-aminocyclopropanecarboxylic acid,
1-aminocyclopropanecarboxylic acid methyl ester,
1-aminocyclopropanecarboxylic acid ethyl ester or
the pharmaceutically acceptable salts thereof.

8. A method for treating major depression in a patient, comprising:

administering to a patient in need thereof an effective amount of a functional antagonist of the N-methyl-D-aspartate (NMDA) receptor complex:

administering to a patient in need thereof an effective amount of a functional antagonist of the N-methyl-D-aspartate (NMDA) receptor complex;

the functional antagonist which is administered being selected from the group consisting of:

1-aminocyclopropylcarboxylic acid;

1-aminocyclopropylcarboxylic acid methyl ester;

1-aminocyclopropylcarboxylic acid ethyl ester; and the pharmaceutically acceptable salts thereof.

9. The method of claim 8, wherein the functional antagonist which is administered is 1-aminocyclopropanecarboxylic acid; or a pharmaceutically acceptable salt thereof.

10. The method of claim 8, wherein the functional antagonist which is administered is 1-aminocyclopropanecarboxylic acid methyl ester.

* * * * *